United States Patent
Gruev et al.

(10) Patent No.: US 11,223,783 B2
(45) Date of Patent: Jan. 11, 2022

(54) MULTISPECTRAL IMAGING SENSORS AND SYSTEMS

(71) Applicant: Washington University, St. Louis, MO (US)

(72) Inventors: Viktor Gruev, Champaign, IL (US); Nimrod Missael Garcia Hernandez, Urbana, IL (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/616,299

(22) PCT Filed: May 22, 2018

(86) PCT No.: PCT/US2018/033919
§ 371 (c)(1),
(2) Date: Nov. 22, 2019

(87) PCT Pub. No.: WO2018/217770
PCT Pub. Date: Nov. 29, 2018

(65) Prior Publication Data
US 2020/0120293 A1     Apr. 16, 2020

Related U.S. Application Data

(60) Provisional application No. 62/509,492, filed on May 22, 2017.

(51) Int. Cl.
*H04N 5/33* (2006.01)
*H04N 9/04* (2006.01)

(52) U.S. Cl.
CPC ......... *H04N 5/332* (2013.01); *H04N 9/04553* (2018.08)

(58) Field of Classification Search
None
See application file for complete search history.

(56) References Cited

U.S. PATENT DOCUMENTS

| | | | |
|---|---|---|---|
| 2006/0087572 A1* | 4/2006 | Schroeder | G02B 5/201 348/272 |
| 2011/0032398 A1* | 2/2011 | Lenchenkov | H01L 27/14627 348/294 |
| 2011/0176577 A1 | 7/2011 | Bandara et al. | |
| 2013/0293871 A1* | 11/2013 | Gruev | G01J 4/04 356/73 |
| 2016/0011050 A1* | 1/2016 | Skauli | G01J 3/36 348/273 |
| 2018/0084167 A1* | 3/2018 | Qian | G01J 3/2803 |

OTHER PUBLICATIONS

International Search Report and Written Opinion, dated Aug. 13, 2018, for International application No. PCT/US2018/033919 (8 pgs).

* cited by examiner

*Primary Examiner* — Talha M Nawaz
(74) *Attorney, Agent, or Firm* — Armstrong Teasdale, LLP

(57) ABSTRACT

A multispectral imaging sensor includes at least one super-pixel including a plurality of pixels. Each pixel includes an imaging element, and each imaging element includes at least one photodetector. Each pixel further includes a spectral filter associated with the imaging element. The spectral filter permits light to pass to its associated imaging element only within a plurality of passbands.

18 Claims, 10 Drawing Sheets

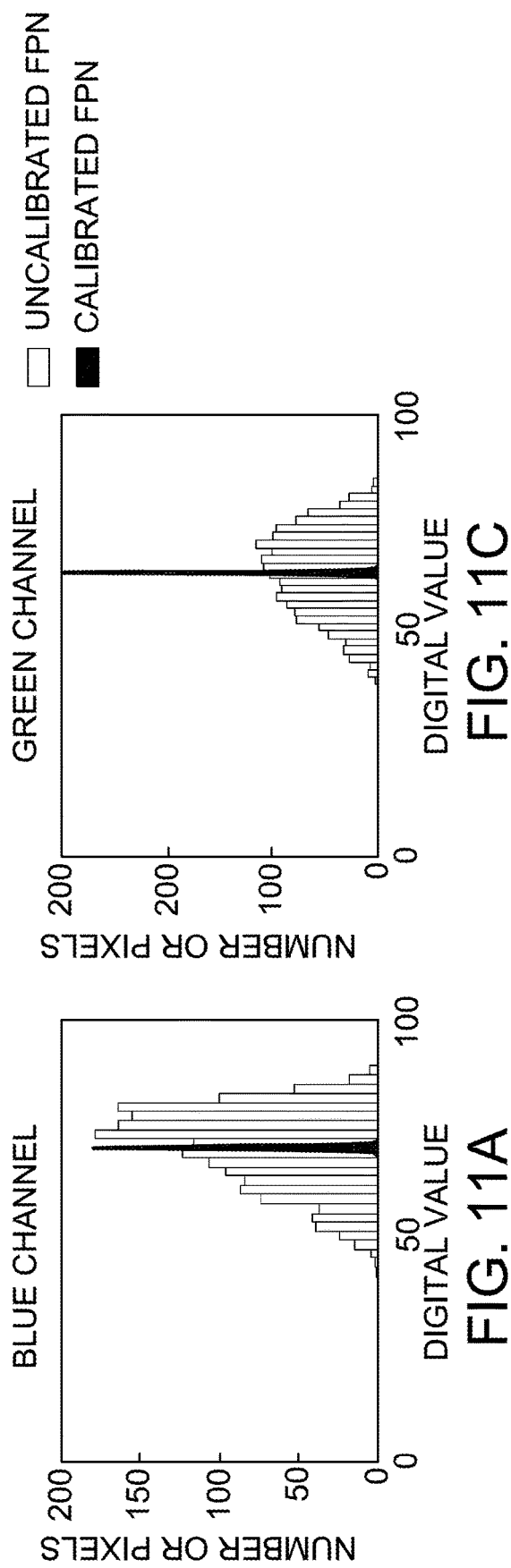
FIG. 11A FIG. 11B FIG. 11C FIG. 11D

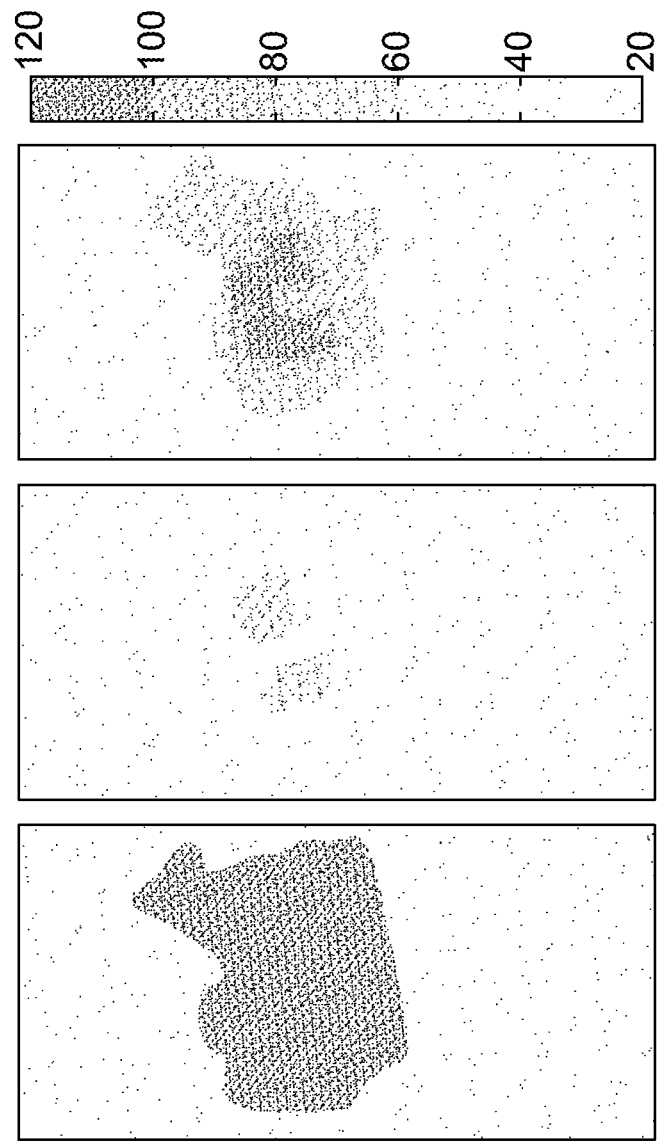

MULTISPECTRAL IMAGING SENSORS AND SYSTEMS

PRIORITY

This National Stage Application claims the benefit of priority to International Application No. PCT/US2018/033919 filed on May 22, 2018, which claims priority to U.S. Provisional Patent Application No. 62/509,492 titled "Multispectral Imaging Sensors and Systems," filed on May 22, 2017, both of which are hereby incorporated herein by reference in their entirety.

STATEMENT REGARDING FEDERALLY SPONSORED RESEARCH & DEVELOPMENT

This invention was made with government support under Grant No. FA95501510348 awarded by the Air Force Office of Scientific Research (AFOSR) and the Defense University Research Instrumentation Program (DURIP). The government has certain rights in the invention.

FIELD

The field of this disclosure relates generally to imaging sensors and, more specifically, to multi-spectral imaging sensors.

BACKGROUND

Some known processes rely solely on imaging of one or more particular spectra of light. For example, fluorescence based imaging relies on either endogenous (i.e. auto-fluorescence) or exogenous molecular markers to extract the location of a targeted tissue. Within the fluorescence based Indocyanine green usage (ICG), near infrared (NIR) fluorescence is of particular interest due to several desirable optical properties of the tissue in this spectrum, including low absorption, low scattering, and low auto-fluorescence in the NIR spectrum. This allows for high signal to background and deep tissue imaging.

Some known imaging systems in, for example, an operating room, rely on multiple cameras and complex optics to separately capture visible and NIR information, leading to bulky and costly instruments.

In another known system, three different complementary metal-oxide semiconductor (CMOS) sensors are used to individually record images from three different spectra. These cameras are connected via a complex set of optical elements, such as beam splitters, relay lenses, mirrors and spectral filters, where each individual element has a different thermal expansion coefficient. During the course of operating the instrument, the various optical parts will contract and expand depending on the temperature in the operating room, local airflow, as well as heating from the light sources and CMOS imagers, or CMOS imaging array. Because there are local temperature gradients in the instrument, real-time software compensation and calibration is generally not feasible.

Miniaturizing an imaging platform capable of recording multispectral information may allow for the wide acceptance and success of multi-spectral imaging modality. A single imaging sensor capable of simultaneously capturing multiple separate spectra of light, including color and/or NIR information, may overcome the disadvantages of some known systems.

BRIEF DESCRIPTION

According to one aspect of the present disclosure, a multispectral imaging sensor includes at least one of superpixel. The superpixel includes a plurality of pixels. Each pixel includes an imaging element and a spectral filter adjacent the imaging element. The imaging element includes a plurality of vertically stacked photodetectors. The spectral filter permits light to pass to its adjacent imaging element only within a plurality of passbands, and the plurality of passbands is a same number of passbands as a number of stacked photo detector assemblies in the imaging element.

According to another aspect of the disclosure, a method of generating a multispectral image using a multispectral imaging sensor includes projecting a target image on an array of the multispectral imaging sensors. The method includes filtering spectral information of the target image. The method includes capturing photons using photodetectors according to respective wavelength passbands of the photodetectors. The method includes converting photons to electric charges. The method includes reassembling an image for each wavelength passband using a processor based on the electric charges.

According to yet another aspect of the disclosure, a system for multispectral imaging includes an imaging sensor and a computing device communicatively coupled to the imaging sensor. The imaging sensor includes at least one superpixel including a plurality of pixels. Each pixel includes an imaging element including a photodetector, and a spectral filter associated with the imaging element. The spectral filter permits light to pass to its associated imaging element only within a plurality of passbands. The computing device is configured to receive electrical signals from each pixel of the imaging sensor and generate an image based on the received electrical signals.

BRIEF DESCRIPTION OF THE DRAWINGS

The embodiments described herein may be better understood by referring to the following description in conjunction with the accompanying drawings.

FIG. 11A is a graph of the uniformity response for a blue pixel of the multispectral imager shown in FIG. 9A before and after calibration.

FIG. 11B is a graphical representation of uniformity response for NIR pixel of the multispectral imager shown in FIG. 9A before and after calibration.

FIG. 11C is a graphical representation of uniformity response for green pixel of the multispectral imager shown in FIG. 9A before and after calibration.

FIG. 11D is a graphical representation of uniformity response for red pixel of the multispectral imager shown in FIG. 9A before and after calibration.

FIG. 12A is a color image obtained during sentinel lymph node (SLN) tracking in a patient with breast cancer using the imaging sensor shown in FIG. 6A.

FIG. 12B is an NIR fluorescence image obtained during SLN tracking in a patient with breast cancer after 1 millisecond (msec) of exposure using the imaging sensor Shown in FIG. 6A.

FIG. 12C is an NIR fluorescence image obtained during SLN tracking in a patient with breast cancer by the imaging sensor shown in FIG. 6A with a 36 millisecond exposure.

DETAILED DESCRIPTION

Figure 1:
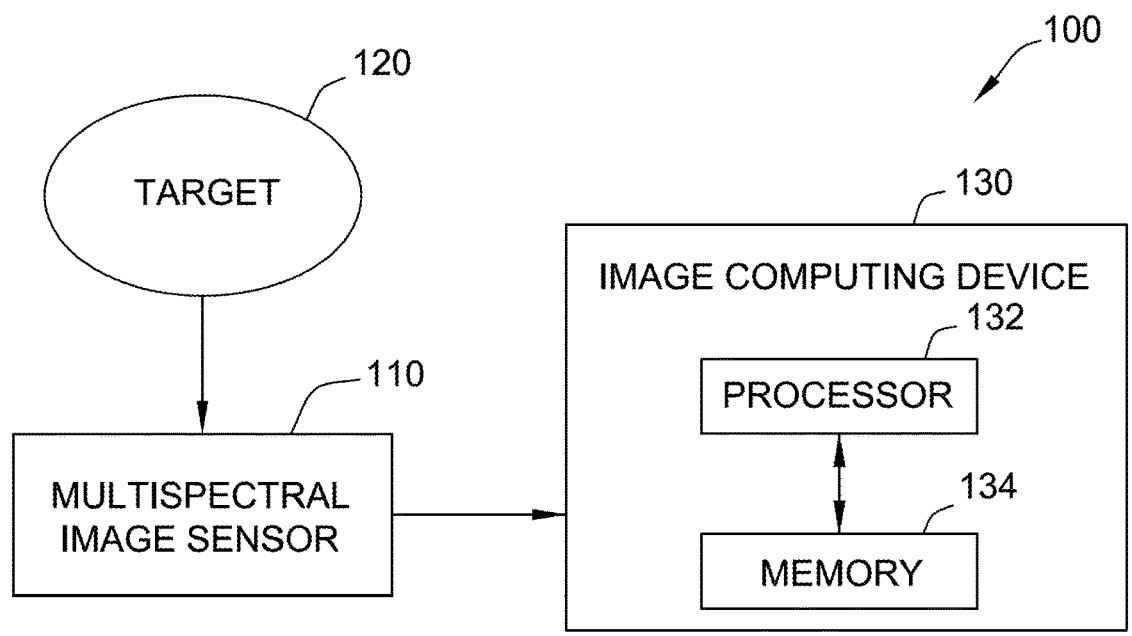
FIG. 1 is a diagram of an example imaging system including a multispectral imaging sensor.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not limit the disclosure, except as outlined in the claims.

Multispectral imaging sensors capable of simultaneously capturing multiple separate spectra of light are described herein. More specifically, a multispectral imaging sensor that is capable of simultaneously-in-time capturing information for multiple spectra of light, visible and/or invisible to the human eye, with high acuity in a condensed structure is disclosed. This enables identification of features of a target that may not be visible in a full spectrum image and/or to the human eye. For example, it enables the detection of anatomical features in a variety of specimens, including but not limited to, human tissue, animal tissue, and/or plant tissue. The example sensors include individual pixels configured to capture different bandwidths of light and generate a plurality of detection signals. Groups of individual pixels are associated with each other in a superpixel. The sensors include multiple superpixels that form an array of superpixels. In example embodiments, each pixel in a superpixel is configured to generate detection signals in response to different spectra of light. Each superpixel is configured to capture the same spectra as each of the other superpixels. The resulting detection signals are able to be translated and read on a computer configured and optimized to generate an image.

The sensor includes two or more types of pixelated filters to limit the light delivered to each pixel to specific wavelengths. In one embodiment, each pixel includes a spectral interference filter positioned on the individual pixel. In another embodiment, each pixel includes multiple spectral interference filters that are vertically stacked on the individual pixel. In the example embodiment, the spectral filters are silicone based. More specifically, the filters are stacked layers of low and high dielectric materials, such as SiO2 and TiO2, selectively positioned on individual pixels in the imaging array. The large difference in dielectric constant results in higher transmission ratios. It should be understood that the materials used to form the filters used in the invention are not limited to SiO2 and TiO2, and may include any other material suitable for a filter used in a sensor.

In some embodiments, each pixel includes vertically stacked photodetectors that simultaneously allow for detection of multispectral wavelengths of light in each pixel in a space-efficient manner leading to high resolution imaging. Each photodetector is adapted to detecting light within a relatively limited band of wavelengths. Generally, shorter wavelengths, such as blue light, are absorbed by the photodetector closer to the surface of the pixel, while longer wavelengths, such as red light, are absorbed by a photodetector farther from the surface of the pixel. Thus, placing photodiode junctions at different depths in the silicon allow different wavelengths to be absorbed. The filter(s) positioned above each pixel limit the wavelengths of light that are allowed to enter each pixel. Specifically, the filter(s) limit the wavelengths of light entering the pixel to narrower bandwidths of light within the bandwidths for which the photodetectors are adapted. For example, a photodetector may be adapted to primarily absorb light having a wavelength between 400 nanometers (nm) and 500 nm. An example filter associated with such a photodetector may only allow light having a wavelength between 400 nm and 410 nm to pass. The filter(s) coupled to a pixel is configured to allow narrower bandwidths of light for each photodetector within the pixel. Thus, for example, a pixel that includes three photodetectors adapted for detecting light within the broad red spectrum, green spectrum, and blue spectrum, will include one or more filters to block all light except a particular, narrow band of wavelengths within the red spectrum, a particular, narrow band of wavelengths within the blue spectrum, and particular, narrow band of wavelengths within the green spectrum. This allows each individual photodetector to absorb and detect a relatively narrow bandwidth of light, and each pixel to absorb and detect three different, relatively narrow bandwidths of light.

In alternative embodiments, each pixel includes a single photodetector that simultaneously allows for detection of multispectral wavelengths of light in each pixel in a space-efficient manner leading to high resolution imaging. In these embodiments, the signal photodetector includes two or more layers with different junction depths, each layer adapted to detecting light within a relatively limited band of wavelengths.

In an example embodiment, nine individual pixels are combined in a three by three, square formation to form a superpixel. Multiple, substantially similar, superpixels are combined to form an imaging array. Each individual pixel includes the spectral filter, and each spectral filter includes three notch pass bands. For example, the filter on the first pixel passes photons at 400 nanometers (nm), 500 nm and 600 nm with a bandwidth of each pass band of about 10 nm. The second pixel passes photons at 420 nm, 520 nm and 620 nm with the bandwidth of each pass band of 10 nm. This sequence of 10 nm increments continues for each subsequent pixel, with the 9th pixel passing photons at 490 nm, 590 nm and 690 nm. This configuration allows twenty-seven 10 nm bands of light to be detected between 400 nm to 690 nm by each superpixel. In another embodiment, a superpixel is formed by organizing the interference filters in a 2-by-2 pixel configuration. For example, using a single photodetector per pixel in a 2-by2 configuration, the filter allows a first pixel to capture red light, a second pixel to capture blue light, a third pixel to capture green light, and a fourth pixel to capture near infrared (NIR) information. Each individual pixel includes the spectral filter, and each pixel can detect three overlapping spectra. This configuration allows twelve spectra to be detected, nine in the visible spectrum and three in the near-infrared spectrum. This filter patterns allows the acquiring of a full resolution color image and NIR fluorescence image, where distinctive shades of near-infrared light are differentiable, at the same spatial location after interpolation.

In an example embodiment, two individual pixels are combined in a one by two, rectangular formation to form a superpixel. Multiple, substantially similar, superpixels are combined to form an imaging array. These superpixels can be spread across the imaging array in a checkerboard fashion, i.e. the two types of superpixels spatially match the location of the black and white tiles of a checkerboard. Each individual pixel includes a spectral filter, and each spectral filter includes a pass band filter. For example, the filter on the first type of pixel passes photons from 400 nanometers (nm) to 650 nanometers (nm), effectively creating a shortpass filter. The second pixel passes photons from 650 nanometers (nm) to 1100 nanometers (nm), effectively creating a longpass filter. This configuration allows six different spectra of light to be detected by each superpixel; three overlapping spectra from 400 nanometers (nm) to 650 nanometers (nm), i.e. visible spectrum, and three overlapping spectra from 650 nanometers (nm) to 1100 nanometers (nm), i.e. near-infrared spectrum. This filter patterns allows the acquiring of a full resolution color image and near-infrared fluorescence image, where distinctive shades of near-infrared light are differentiable, at the same spatial location after interpolation.

In some embodiments, the imaging system is trained to identify multiple near-infrared fluorescence dyes with different excitation-emission spectra. For example, a first fluorescence dye with excitation at 660 nanometers (nm) and emission at 680 nanometers (nm), a second fluorescence dye with excitation at 780 nanometers (nm) and emission at 800 nanometers (nm), and a third fluorescence dye with excitation at 880 nanometers (nm) and emission at 900 nanometers (nm), are used to track and label three different cell types. A machine learning algorithm, such as linear classification, logistic regression, or linear regression is used to train the imaging system into recognizing the different near-infrared fluorescent dyes used based on the spectral proportions of light captured by the pixels with near-infrared spectral filters. Different shades of near-infrared light are associated with the particular emission of light of the different fluorescent dyes used in a specific application.

In an example embodiment, the imaging sensor is a complementary metal-oxide semiconductor (CMOS) imaging array. In this embodiment the imaging sensor is a short epitaxial layer of microns together with vertical trenches between pixels, implemented using an n+ doped silicon, eliminating the optical crosstalk between pixels. In other embodiments, a different type of image sensor is used, such as but not limited to, a semiconductor charged-coupled device (CCD) and/or N-type metal-oxide-semiconductor (NMOS) technology.

In some embodiments, the pixels and the photodetectors can be programed, such as through the use of a computer, to have different integration times. For example, to ensure that pixels or photodetectors imaging a spectral band with low photon flux have a high signal-to-noise ratio (SNR) image, the integration (i.e. exposure) time is set to be longer compared to pixels or photodetectors imaging spectral bands with high photon flux. Dedicated registers in the imaging sensor allow pixels to be individually reset and, hence, have a variable integration time as set by a user. Moreover, signals generated by each pixel, and each photodetector within the pixel, may be individually retrieved and processed, allowing precise determination of the amount of light in each bandwidth detected by the imaging sensor.

In an example embodiment, the multispectral imaging sensor is used in an operating room to track sentinel lymph nodes (SLN) in patients with breast cancer and a nervous network. In this embodiment, tumor and nerve targeted near-infrared dyes having different excitation-emission spectra are injected to the patient.

For example, the multispectral sensor may be mounted on endoscope optics (i.e., either mounted on the tip of an endoscope so that sensor is inserted into a body or mounted at the end of the endoscope relay optics so that the sensor remains outside of the body) so that the surgical site can be monitored indirectly by a surgeon. Multispectral images of the gall bladders and surrounding tissues are captured by the sensor across many patients, providing a training dataset from which further information can be extracted. To facilitate classification of tissues, supervised learning can be carried out in which an expert manually labels a hyperspectral image with the tissue type and an algorithm learns the relationship between the spectral features in the multispectral images and the tissue types. To classify unknown tissues, a machine learning algorithm such as support vector machine (SVM) or artificial neural network (ANN) maybe used to compare unknown spectral features in multispectral images with the previously derived relationship.

Alternatively, principle component analysis may be used to extract principle components capable of capturing variability between tissue types, and each pixel of the multispectral image is compared to the principle components in order to determine the most likely classification. The multispectral sensor may further be equipped to detect near infrared light, which penetrates deeper than visible light. This embodiment can be used for a classification process capable of differentiating between the gall bladder and obscured bile ducts without additional dyes. The ability to identify different shades of near-infrared light allows the accurate identification of the location of the near-infrared dyes, effectively labeling human tissue as nerve or tumor tissue. In another example embodiment, near-infrared dyes that bond to plasma and lymphatic fluid, with different excitation-emission spectra, are used to track blood perfusion and lymphatic nodes, respectively, simultaneously. Examples of dyes include, but not limited to, are indocyanine green and/or methylene blue dyes.

For example, fluorescent dye, such as indocyanine-green, can be injected into the bile ducts reducing the chance of a misclassification as well as the risk of complications. It should be noted that a nerve targeted dye has an excitation spectra at 660 nanometers (nm) and an emission spectra at 680 nanometers (nm) while a tumor targeted dye has an excitation spectra at 780 nanometers (nm) and an emission spectra at 800 nanometers (nm).

In some embodiments, the multispectral imaging sensor is used in an agricultural setting to examine the agricultural products. Agricultural product include, but are not limited to, meats, fruits, and grains. For example, maize, an agricultural product which is consumed by humans, used as feedstock, and prepared as seed, is susceptible to infection by toxigenic fungi of the genera *Fusarium* and *Aspergillus* while growing in the field and being processed after harvest. Once detected, the fungi-carrying maize kernels can be discarded to avoid consumption by humans and other animals.

For example, in one embodiment, the sensor may be mounted on microscope optics to examine individual maize kernels in the laboratory as a part of a manual quality control process. In another embodiment, the sensor may be mounted with other equipment to examine bulk maize kernels at the assembly line as part of an automatic quality control process. Hyperspectral images of non-infected and infected kernels can be captured by the sensor and spectral features can be extracted and aggregated to construct models for both classes of kernels using a computer. Unknown kernels may then be classified by capturing hyperspectral images, extracting spectral features, and comparing the results to the constructed models using statistical methods or machine learning. Similar methods can be used to evaluate the hardness of maize kernels by examining the presence of glassy and floury endosperm and to discriminate between varieties by examining the difference in reflectance spectra.

In some embodiments, the multispectral imaging sensor is used in an agricultural setting to study the growth and development of various crops across both space and time. For example, precision agriculture requires that crop data be collected for each crop field during each part of the crop growing season, analyzed to determine how plants react to spatially and temporally local environmental factors, and applied to determine the optimal application of inputs, such as water and fertilizers, to offset environmental factors.

For example, the sensor may be mounted to either an airborne vehicle, such as an aircraft or a drone, that flies over the crop fields or a ground-based vehicle, such as a truck, that drives through the crop fields. Crop yield can be predicted and, as a result, may be used to target inputs, such as water and fertilizer. Hyperspectral images of the field are collected between planting time and harvesting time, and instrumentation mounted on a combine can be used to measure crop yield at harvest time. Spectral features can be extracted from the multispectral images detected by the sensor, and regression can be used to construct a model that maps spectral features at a specific instant in time or across various durations of time to the final crop yield.

Additionally, multispectral imaging using the sensor can be used as a raw input to agricultural models that attempt to relate the spectral information to meaningful quantities that can be traced back to crop yield. Multispectral images of the crop field are collected using the sensor, and intensity values can be converted to reflectance values using appropriate calibration data. The reflectance values are then used to compute vegetation indices (i.e., the traditional normalized difference vegetation index (NDVI) or the more modern two-band vegetation index (TBVI)), and the vegetation indices can either be used to predict crop yield or determine other vegetation features. Vegetation features include, but are not limited to, leaf area and/or biomass, and may be used to predict yield indirectly using analytical or empirical models.

In some embodiments, the multispectral imaging sensor is used to detect and differentiate between healthy and diseased tissues by recording changes in tissues during disease progression. For example, peripheral artery disease (PAD) occurs when plaque builds up in any artery that does not supply the heart or brain, causing a reduction in blood flow to the extremities that may result in tissue death as well as complications that may result in life-threatening coronary artery disease or cerebrovascular disease. This reduced blood flow results in reduced oxygen flow, manifesting in variable concentrations of oxygenated hemoglobin and deoxygenated hemoglobin near the site of the occlusion.

For example, the multispectral sensor may be mounted to a handheld device enabling a physician to capture information about the amount of oxyhemoglobin, deoxyhemoglobin, and oxygen in the blood. Since oxyhemoglobin and deoxyhemoglobin have characteristic reflectance spectra with oxyhemoglobin exhibiting twin peaks at 541 nm and 576 nm and deoxyhemoglobin exhibiting a single peak at 555 nm, the multispectral sensor is used to capture the reflectance spectra for both types of hemoglobin as a reference, and multispectral images may be captured near the termination of major arteries in the extremities where PAD should be most obvious in the patient. The spectrum at each point in the patient image can be represented using the reference image as a sum of an oxyhemoglobin part, a deoxyhemoglobin part, and a residual part, and regression can be used to compute the amount of oxyhemoglobin and deoxyhemoglobin as well as the amount of oxygen in vivo. Depending on several factors, one of these quantities may be identified as a better marker for PAD (i.e., the amount of oxyhemoglobin or the deoxyhemoglobin), and if a model mapping the quantity to the severity of PAD is constructed from empirical data, these results can be used with classification techniques to determine if a patient has PAD and can be used with regression techniques to determine the severity of the PAD. Similar methods can be used to identify abnormal angiogenesis that may be associated with tumor development, providing more opportunities for cancer diagnosis.

Using the interference configurations, the multispectral imaging sensor can capture various bands of light with different exposure (integration) times, leading to high SNR images from each spectra.

In some embodiments, each spectral filter is formed using physical vapor deposition (PVD) to alternatively deposit layers of low dielectric material and high dielectric material on the surface of the multispectral imaging sensor. Low dielectric materials may include but are not limited to $SiO2$ or $HfO2$. High dielectric materials may include but are not limited to $TiO2$ or $HfSiO$. The spectral filters are pixelated and match the pitch of the underlying pixels. In other embodiments, other materials and/or deposition techniques may be used to form the spectral filter.

FIG. 1 is a diagram of a system 100 including a multispectral imaging sensor 110. Imaging sensor 110 is configured to receive light reflected from a target 120 and output electrical signals corresponding to the reflected light received by the sensor 110. Imaging sensor 110 is configured to capture and generate signals for multiple bands of wavelengths of light from target 120.

Imaging sensor 110 is communicatively coupled to an image computing device 130. Image computing device 130 includes any computing device capable of receiving the electrical signals generated in imaging sensor 110 and analyzing the electrical signals. Moreover, imaging computing device is configured control the capture of image information with the imaging sensor 110, including controlling the exposure time of one or more pixels of imaging sensor 110. In some embodiments, the computing device 130 is configured to generate an image of the target 120 based on the electrical signals. In some embodiments, the computing device 130 combines (e.g., spatially interpolates) data from multiple pixels and/or multiple photodetectors to create the image. In some embodiments, computing device 130 bases the generated image on less than all of the electrical signals from imaging sensor. For example, computing device 130 may generate an image based only on the electrical signals associated with red wavelengths of light, infrared wavelengths of light, etc. Moreover, computing device 130 may generate multiple images, such as an image based on all electrical signals from imaging sensor 110, separate images each based only on signals associated with a single wavelength of light, images based on signals associated with various combinations of spectra, etc. Image computing device 130 includes at least one processor 132 in communication with a memory 134.

Figure 2:
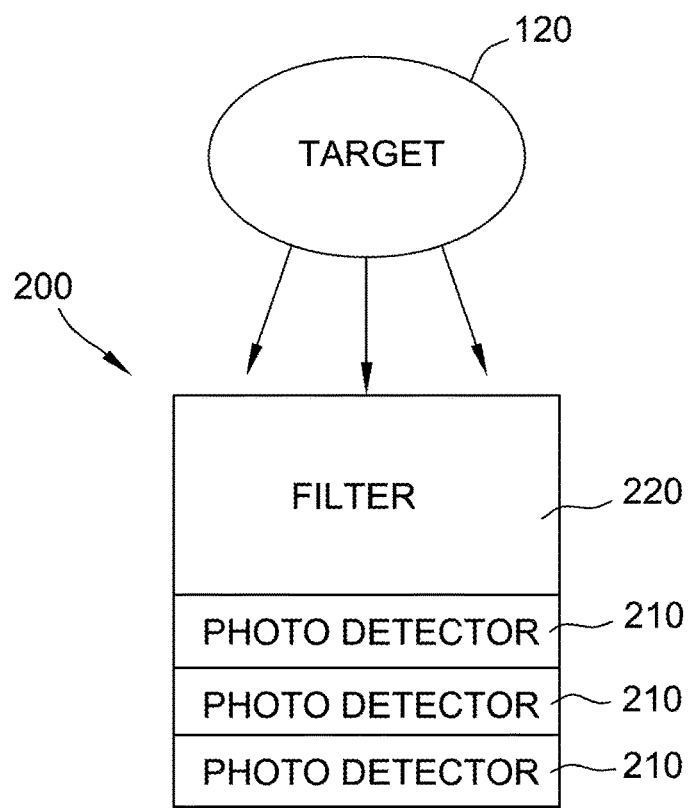
FIG. 2 is a diagram of a cross section of a single pixel useable in the multispectral imaging sensor shown in FIG. 1.

FIG. 2 is a block diagram of a cross-section of an example of a single pixel 200 included within the multispectral imaging sensor 110 shown in FIG. 1. Photodetectors 210 (e.g., photodiodes) are stacked on top of one another in a vertical configuration within each pixel 200. In the example embodiment, photodetectors 210 are integrally formed. In other embodiments, pixel 200 may include more or fewer photodetectors than the number illustrated in FIG. 2, including one photodetector. Moreover, in other embodiments, pixel 200 may include more than one spectral filter 220.

Figure 3:
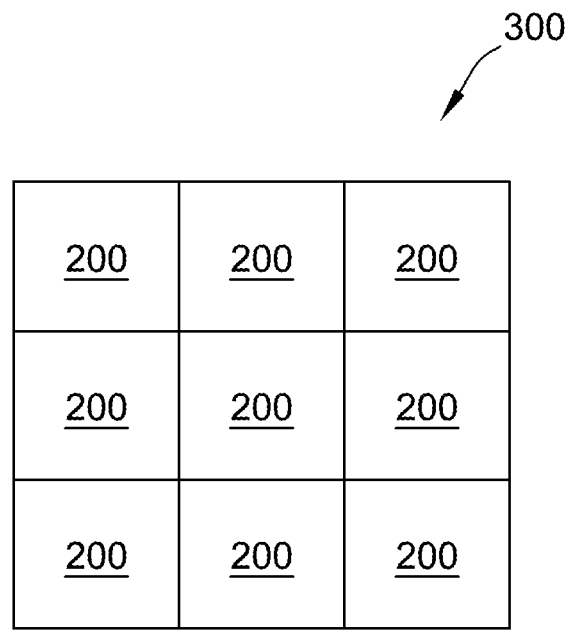
FIG. 3 is a diagram of a superpixel formed from a plurality of the pixels shown in FIG. 2.

FIG. 3 is a diagram of a superpixel 300 formed from a plurality of pixels 200 shown in FIG. 2. In the example embodiment, superpixel 300 is a three by three formation of pixels 200. In another embodiment, superpixel 300 is a two by two formation of pixels 200. In the example embodiment, each pixel 200 in the superpixel 300 is configured to detect light at a different plurality of wavelength bands from each other pixel 200 in the superpixel 300. For example, filter 220 on a first pixel 200 passes photons at 400 nm, 500 nm, and 600 nm with bandwidth of each pass band of about 10 nm. A second pixel 200 in superpixel 300 detects photons at 410 nm, 510 nm and 610 nm with the bandwidth of each pass band of 10 nm. This sequence of 10 nm increments continues for each subsequent pixel 200 in superpixel 300, with a 9th pixel 200 of superpixel 300 detecting photons at 490 nm, 590 nm and 690 nm. This configuration allows twenty-seven 10 nm bands of light to be detected between 400 nm to 690 nm by each superpixel 300. In other embodiments, at least one filter 220 passes photons at different bandwidths than the filter 220 for one or more other pixels 200. In some embodiments, one or more pixels 200 in superpixel 300 includes a filter 220 that passes light at one or more of the same wavelengths as at least one filter 220 for another pixel 200 in superpixel 300.

In another embodiment, a superpixel 300 is formed by organizing the spectral filters 220 in a 2-by-2 pixel configuration. For example, filter 220 allows pixel 200 to first capture red light, second pixel 200 to capture blue light, third pixel 200 to capture green light, and fourth pixel 200 to capture near infrared (NIR) information. This filter pattern allows the acquiring of a full resolution color image and NIR fluorescence image at the same spatial location after interpolation.

Figure 4:
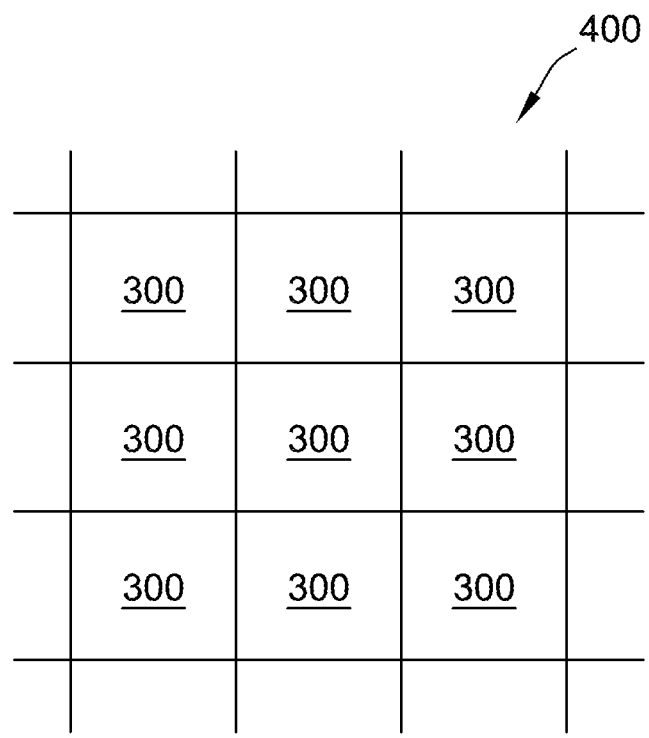
FIG. 4 is a diagram of an imaging array formed from a plurality of superpixels shown in FIG. 3.

FIG. 4 is a diagram of a pixel array 400 formed from a plurality of superpixels 300 shown in FIG. 3. In the example embodiment, pixel array 400 is implemented as a CMOS image sensor. Alternatively, pixel array 400 may be implemented as a charge coupled device, an N-type metal-oxide-semiconductor, or any other suitable sensor. In the example embodiment, superpixels 300 are identical to each other in formation and/or configuration within the same pixel array 400. In other embodiments, superpixels 300 may differ from each other in formation and/or configuration within the same pixel array 400.

Figure 5:
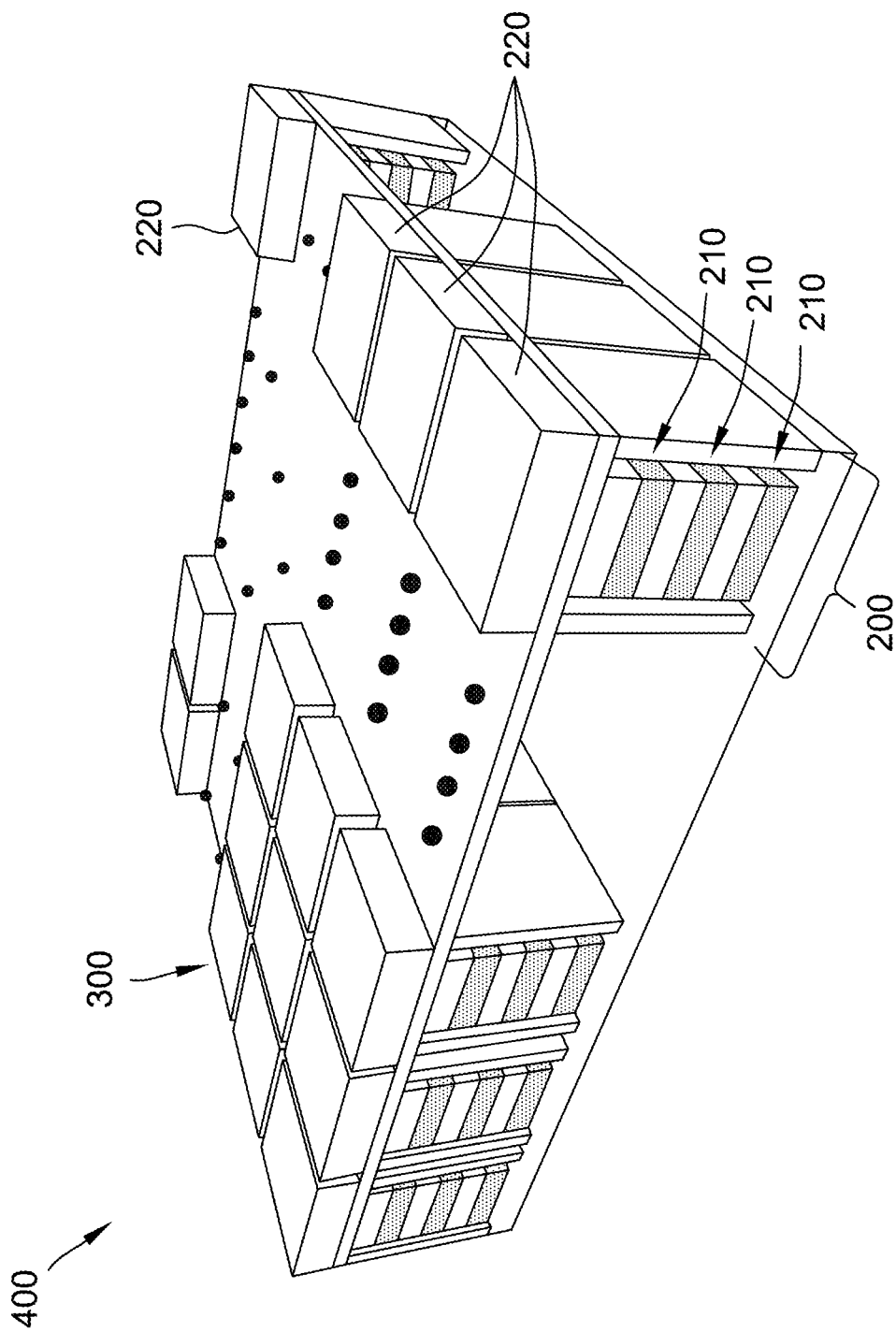
FIG. 5 is a perspective view of an example multispectral imaging sensor with pixelated spectral filters.

FIG. 5 is a perspective view of an example embodiment of multispectral imaging sensor 110. Sensor 110 includes pixel array 400 and spectral filters 220. Incoming light is filtered through at least one pixelated spectral filter 220 before reaching a plurality of photodetector assemblies 210, as described in more detail herein. In the example embodiment, spectral filters 220 are vertically stacked on top of photodetectors 210. Sensor 110 is divided into a plurality of pixels 200 and a plurality of superpixels 300. In the example embodiment, each superpixel 300 includes nine pixels 200. Alternatively, superpixels 300 may include any number of pixels 200 that enable sensor 110 to function as described herein.

Using the combination of spectral filter 220 and photodetector 210 assemblies, sensor 110 can simultaneously acquire spectral information with a relatively high spatial and temporal resolution. Further, sensor 110 is relatively compact, lightweight, and robust.

In the example embodiment, each pixel 200 includes one spectral filter 220 and three photodetectors 210. Each photodetector 210, or photodetector assembly 210, is capable of detecting light and converting the detected light into electrical signals. In the example embodiment, each pixel 200 is capable of detecting three bandwidths of light, e.g., red light, green light, and blue light. Alternatively, or additionally, photodetector assemblies 210 may be configured to detect more than three colors, or ranges of wavelengths. It should be appreciated that sensor 110 may include any number of pixels 200, with any suitable pixel pitch, that enables sensor 110 to function as described herein.

In the example embodiment, each photodetector 210 is formed by alternatively stacking different types of conductive type regions. For example, the first layer contains a particular conductive type such as positive-doped material. The second layer contains a conductive type material that is opposite to the first one. In this embodiment, the second layer is negatively doped material. The third layer contains a conductive type material that is opposite to the second one and so on. The alternative stacking of different types of conductive materials can be achieved via several different fabrication procedures, including but not limited to doping, epitaxial grown material, deposition and other.

It should be understood that multispectral imaging sensor 110 will be associated with appropriate circuitry for signal conditioning, processing, amplifying, readout, etc. that is not shown in FIGS. 1-5. Such circuitry may be included as part of imaging sensor 110, as separate component(s) in system 100, or included within another component of system 100.

Figure 6:
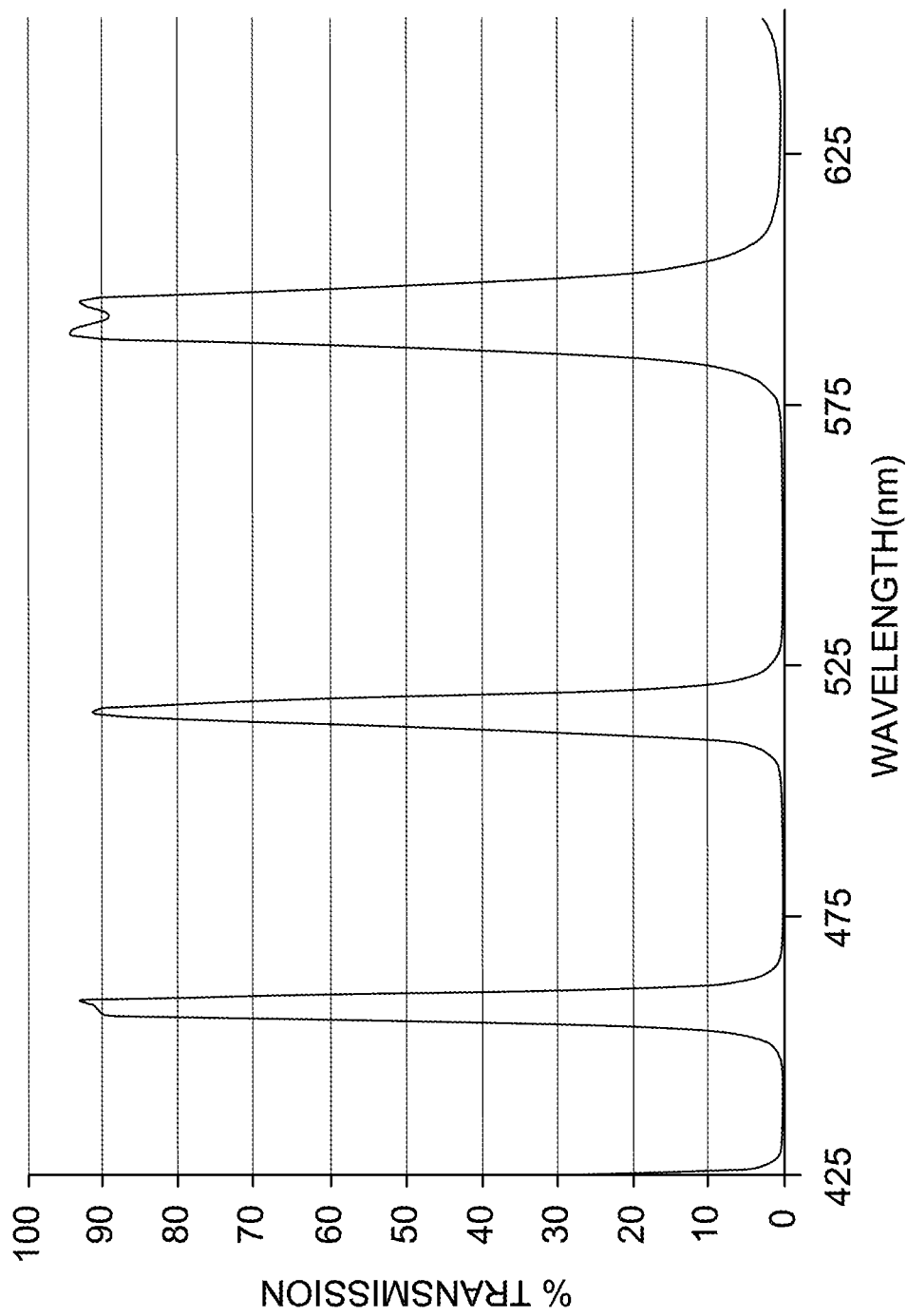
FIG. 6 is a line graph of the spectral response of a single pixel of the imaging array shown in FIG. 4.

FIG. 6 is a line graph showing the spectral response of a single pixel 200 of the multispectral imaging sensor 110 shown in FIG. 5. The filter 220 associated with the pixel 200 of FIG. 6 included three passbands centered at about 460 nm, 510 nm, and 590 nm. The filters were fabricated through deposition of various alternating high-low dielectric materials. The spectral filter was then pattern and the size of the filter is 10 microns by 10 microns. The filter was illuminated with monochromatic light and the transmitted light was recorded with calibrated photodetectors.

Figure 7:
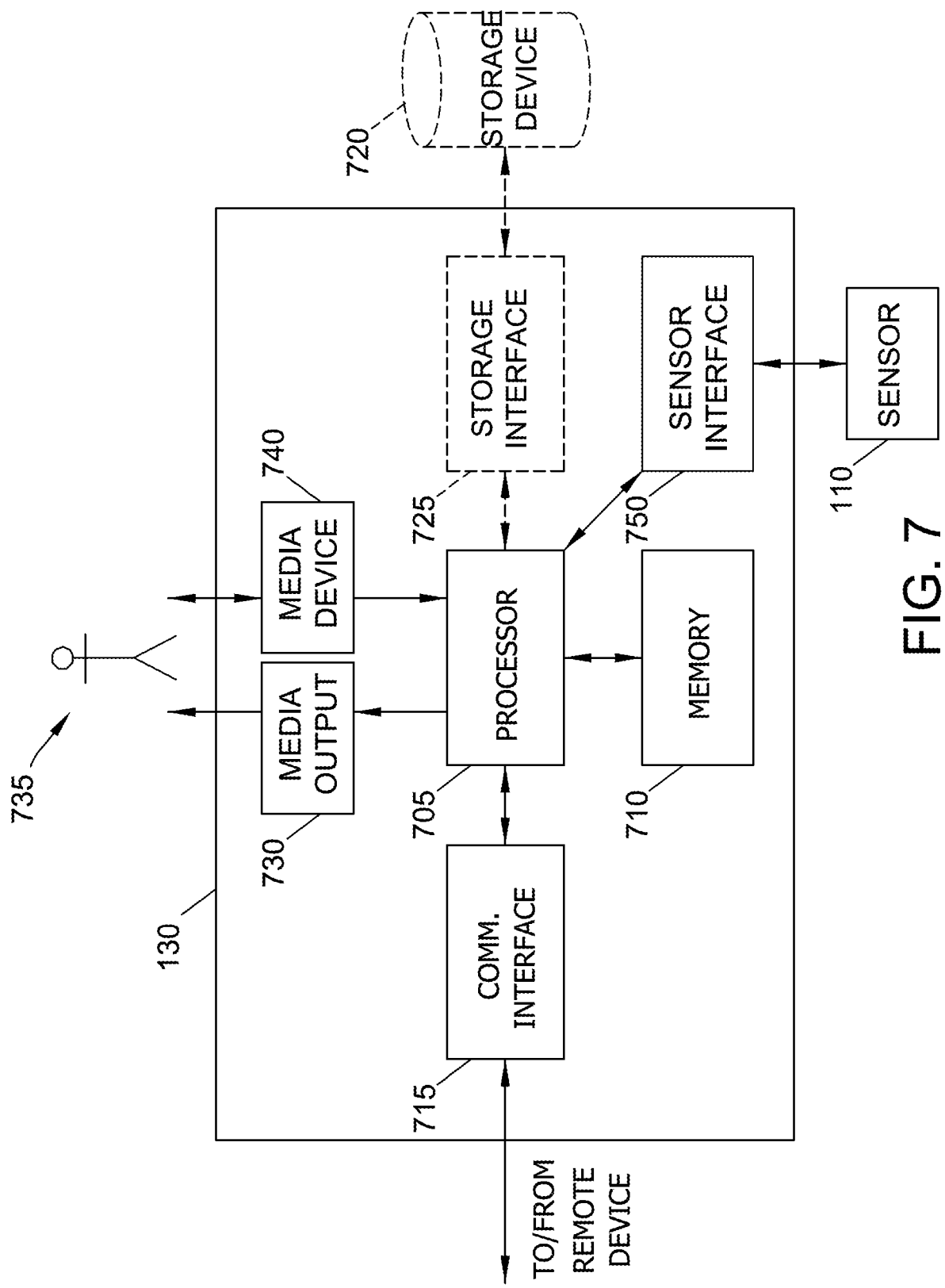
FIG. 7 is an example computing device for use with the sensor in shown FIG. 4.

FIG. 7 is example computing device 130 for use in system 100 (shown in FIG. 1). Computing device 130 includes a processor 705 for executing instructions. Instructions may be stored in a memory area 710, for example. Processor 705 may include one or more processing units (e.g., in a multi-core configuration) for executing instructions. The instructions may be executed within a variety of different operating systems on the computing device 130, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C #, C++, Java, or other suitable programming languages, etc).

Processor 705 is operatively coupled to a communication interface 715 such that computing device 130 is capable of communicating with a remote device such as a user system or another computing device 130. Communication interface 715 may include, for example, a wired or wireless network adapter or a wireless data transceiver for use with a mobile phone network, Global System for Mobile communications (GSM), 3G, or other mobile data network or Worldwide Interoperability for Microwave Access (WIMAX).

Processor 705 may also be operatively coupled to a storage device 720. Storage device 720 is any computer-operated hardware suitable for storing and/or retrieving data. In some embodiments, storage device 720 is integrated in computing device 130. For example, computing device 130 may include one or more hard disk drives as storage device 720. In other embodiments, storage device 720 is external to computing device 130 and may be accessed by a plurality of computing devices 130. For example, storage device 720 may include multiple storage units such as hard disks or solid state disks in a redundant array of inexpensive disks (RAID) configuration. Storage device 720 may include a storage area network (SAN) and/or a network attached storage (NAS) system.

In some embodiments, processor 705 is operatively coupled to storage device 720 via a storage interface 725. Storage interface 725 is any component capable of providing processor 705 with access to storage device 720. Storage interface 725 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 705 with access to storage device 720.

Computing device 130 may also include at least one media output component 730 for presenting information, e.g., images, to a user 735. Media output component 730 is any component capable of conveying information to user 735. In some embodiments, media output component 730 includes an output adapter such as a video adapter and/or an audio adapter. An output adapter is operatively coupled to processor 705 and operatively couplable to an output device such as a display device, a liquid crystal display (LCD), organic light emitting diode (OLED) display, or "electronic ink" display, or an audio output device, a speaker or headphones.

In some embodiments, computing device 130 includes an input device 740 for receiving input from user 735. Input device 740 may include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output device of media output component 730 and input device 740.

Computing device 130 includes a sensor interface 750 for operatively and/or communicatively coupling processor 705 to sensor 110. Sensor interface 750 may include any interface, bus, interconnect, communication gateway, port, and/or any other component capable of providing processor 705 with access to sensor 110.

Memory area 710 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

Stored in memory area 710 are, for example, computer readable instructions for providing a user interface to user 735 via media output component 730 and, optionally, receiving and processing input from input device 740, sensor interface 750, and/or sensor 110. A user interface may include, among other possibilities, an image viewer and client application. Image viewers enable users, such as user 735, to display and interact with media and other information received from sensor 110. A client application allows user 735 to interact with sensor 110, e.g., requesting a frame to be captured.

Figure 8:
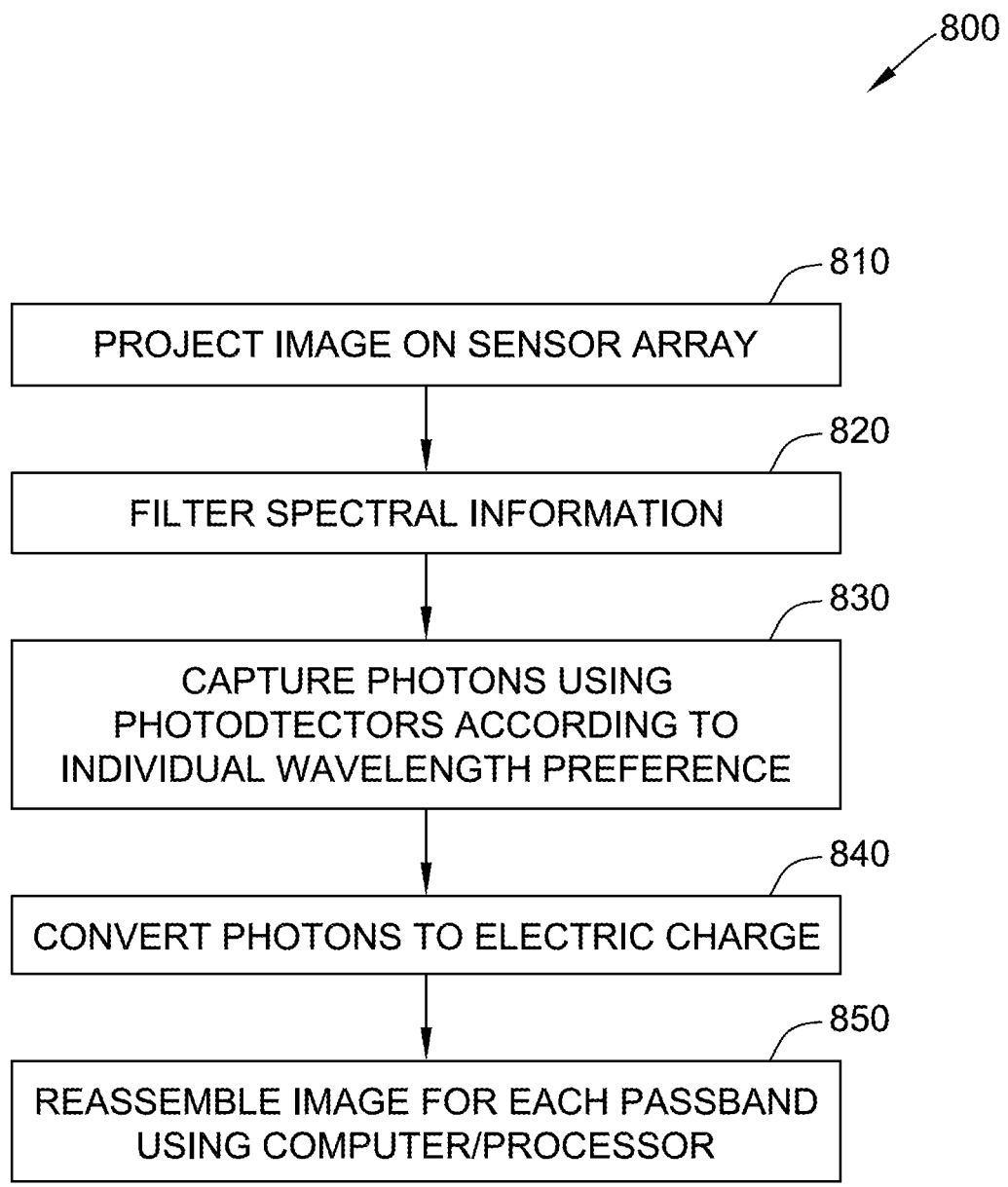
FIG. 8 is an example method for use of the sensor shown in FIG. 4.

FIG. 8 is a flowchart 800 an example method of using a multispectral sensor, such as sensor 110. More particularly, flowchart 800 illustrates a method for simultaneously capturing multiple separate spectra of light, including color and/or NIR information. Initially, an image is projected 810 upon sensor 110. More particularly, photons are received by pixel array 400. The spectral response of pixel array 400 may be non-linear. In addition, the responsivity curve of pixel array may include areas of overlap. Spectral information is filtered 820 using plurality of spectral filters. Each filter is a passband filter allowing a plurality of discrete bandwidths of light to pass to the photodetectors. Sensor 110 captures 830 photons using photodetectors. Photons are converted 840 to an electric charge, and reassembled into an image 850, visible to the human eye, for each passband using a computer and/or processor, such as computing device 130.

In the example of FIG. 8, steps 810-850 are illustrated in sequential order. However, it should be appreciated that flowchart 800 illustrates non-limiting examples of operations. For example, two or more operations of the steps 810-850 may be executed in a partially or completely overlapping or parallel manner. In other examples, operations may be performed in a different order than that shown. Further, additional or alternative operations may be included. Moreover, more than one iteration of steps 810-850 may be performed, e.g., to capture video, i.e., sequential frames, using sensor 110.

Figure 9A:
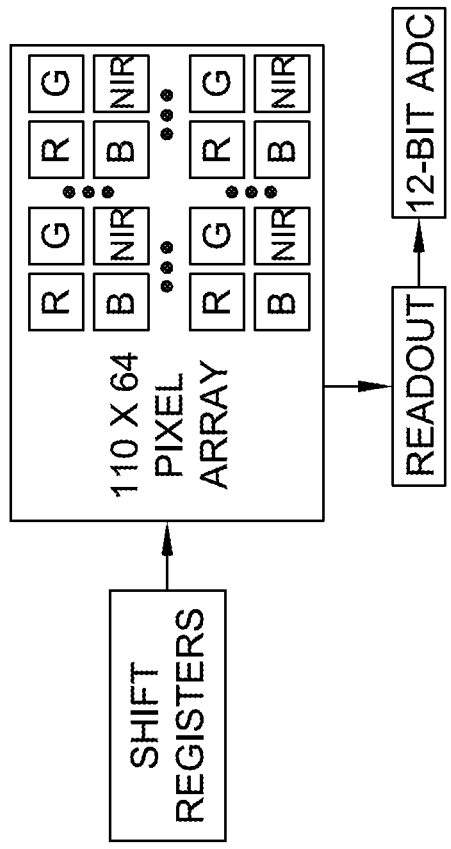
FIG. 9A is a block diagram of an example pixelated multispectral imager in a 2-by-2 configuration.
Figure 9B:
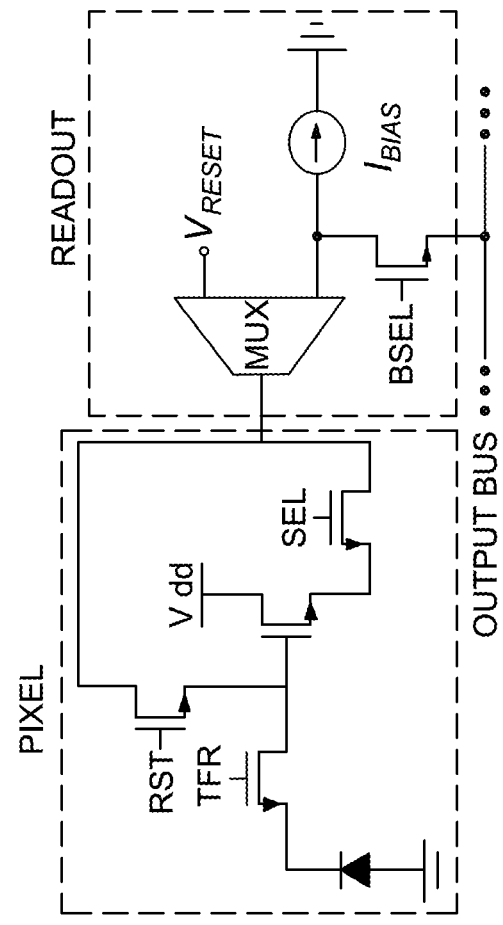
FIG. 9B is a diagram of a pixel and readout circuit associated with the multispectral imager shown in FIG. 9A.

FIG. 9A is a block diagram of another multispectral imaging sensor including a pixelated CMOS image sensor in a 2-by-2 configuration. FIG. 9B is a diagram of a pixel and readout circuit schematic associated with the CMOS image sensor and pixel configuration as shown in FIG. 1. The pixel is composed of a pinned photodiode and 4 transistors including reset, charge transfer, source follower and address transistor. The reset potential bus and the read-out bus are shared to reduce the pixel pitch and increase the pixel's fill factor. Peripheral circuitry control whether the pixel output bus is connected to Vdd-Vth potential during the reset phase or to a current source during the read-out phase. All pixels are first reset, and then read-out after the reset phase. After a short integration time, the charge transfer transistor is turned on and charges accumulated on the pinned photodiode are transferred to the floating diffusion node. After the charge transfer is completed, all visible spectrum pixels are read-out. After a longer integration time, the charge transfer transistor is turned on again, and only the NIR pixels are read-out from the imaging array.

In an operating room setting, the different integration time of the visible and NIR pixels may be important due to the fact that the minimum visible spectrum illumination as required by the Food and Drug Administration (FDA) and European Medical Agency (EMA) is 40,000 lux. Moreover, due to the high illumination intensity in the operating room, only short integration time is needed to produce an acceptable color image. The exposure time for all NIR pixels is set to 36 milliseconds (ms) to ensure 28 frame per second (fps) imaging rate to maximize the SNR of the NIR image, and the integration time for the visible spectrum pixels is set to 1 ms to avoid saturated color image. It should be noted that the integration times for both sets of pixels can be changed depending on the illumination conditions.

EXAMPLES

Example 1: Detecting the Fluorescence of ICG Accumulation in Sentinal Lymph Node on Patients with Breast Cancer An imaging sensor similar to FIGS. 9A and 9B was constructed with a pixel array and individual pixels in a two by two formation, and used in an operating room to provide real-time feedback to the surgeon regarding the location of the sentinel lymph nodes in patients with breast cancer without disturbing the surgical workflow of the surgeon. The imaging technique was used in 3 patients and 7 SLN were identified using NIR fluorescence information obtained by the sensor.

Figure 10:
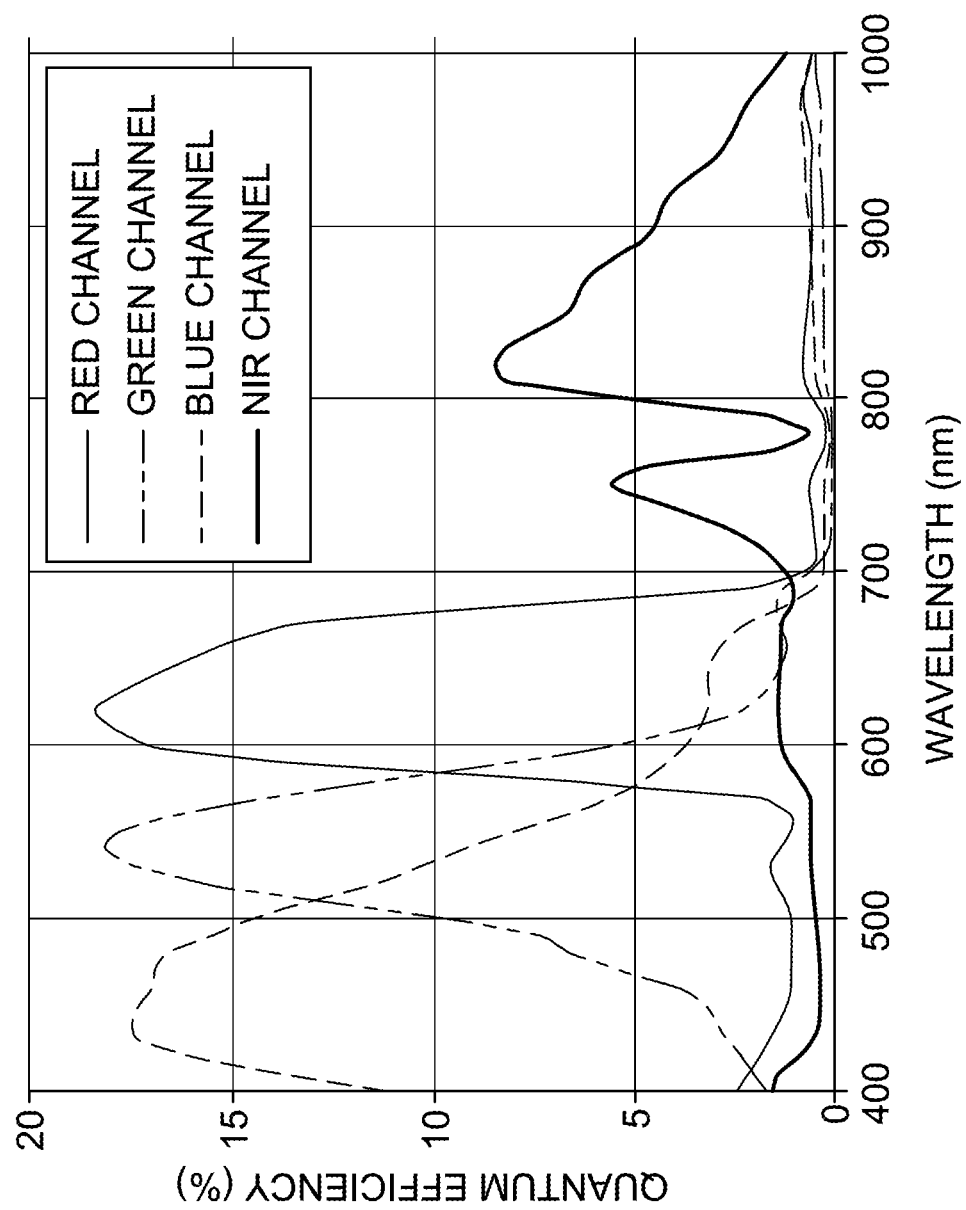
FIG. 10 is a line graph of the quantum efficiency for pixels of the multispectral imager shown in FIG. 9A.

The sensor's optical properties were evaluated using a monochromator combined with an integrating sphere. The monochromator wavelengths were swept from 400 nm to 1100 nm in steps of 10 nm. FIG. 10 is a graph of the quantum efficiency for each of the four base pixels from the CMOS imager. The blue, green, and red filters have quantum efficiency (QE) peaks of ~18% at wavelengths of approximately 450, 550, and 625 nm respectively. The NIR pixel has peak QE at 805 nm of 8.5%, which matches the peak emission wavelength of Indo Cyanate (ICG) dye used during surgery. The sensor also contains an additional notch filter at 780 nm to block the excitation light for ICG fluorophores.

The fixed pattern noise for the four different pixels is ~15% before calibration and 0.8% after calibration, as shown in FIG. 11A-11D. The spatial variation in the optical response across the imaging array is primarily due to the variation of the thickness of the dielectric layers comprising the interference filters and can be mitigated by more precise dielectric layer deposition.

FIGS. 12A-12C presents images of SLN tissue resected from one patient and displayed on a monitor to the surgeon. The color images recorded by the sensor provide information about the anatomical features of the patient, while the NIR image provides information about the location of the sentinel lymph nodes. Since both images are inherently coregistered, the physician is able to easily identify the anatomical features that need to be resected with the help of the NIR information, as well as health tissue that needs to be preserved. When the exposure time is set the same for the visible and NIR pixels, i.e. 1 ms, the color image shows good contrast between the various regions in the SLN as well as the surrounding tissue. When the exposure time for both the visible and NIR pixels is decoupled and the NIR exposure time is set to 36 ms, a brighter NIR image is obtained and the location of the sentinel lymph nodes is accurately determined and resected. Since the exposure time is optimized for both color and NIR pixels separately, a high contrast color image and high contrast NIR image were obtained during the surgical procedure were presented to the physician. Radioactive tracers were used to identify the SLN relays, which identified 5 SLN. Visible dyes were also used to identify SLN relays, which identified 6 SLN. The fluorescence imaging technique showed higher sensitivity then both radioisotopes and visible dyes. Moreover, the NIR light used for exciting ICG tracers are non-ionizing, providing higher safety to the both the patient and the care giver, i.e. the surgeon.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present disclosure have been described in detail, it will be understood by those skilled in the art that various modifications can be made therein without departing from the spirit and scope of the disclosure as set forth in the appended claims.

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A multispectral imaging sensor comprising:
   at least one superpixel including a plurality of pixels, wherein each pixel of the plurality of pixels comprises:
   an imaging element including a plurality of photodetectors; and
   a spectral filter attached to the imaging element, wherein the spectral filter has a plurality of passbands and permits light to pass to only the imaging element to which it is attached and only within a plurality of passbands.

2. The multispectral imaging sensor of claim 1, wherein for each pixel the plurality of passbands comprises a same number of passbands as a number of photodetectors in the imaging element.

3. The multispectral imaging sensor of claim 1, wherein the plurality of photodetectors of each imaging element comprises a plurality of vertically stacked photodetectors.

4. The multispectral imaging sensor of claim 3, wherein the plurality of photodetectors of each imaging element comprises three vertically stacked photodetectors.

5. The multispectral imaging sensor of claim 1, wherein the spectral filter of each imaging element comprises layers of low dielectric material and high dielectric material alternatively deposited on its imaging element.

6. The multispectral imaging sensor of claim 1, wherein the plurality of pixels comprises nine pixels in a three pixel by three pixel arrangement.

7. The multispectral imaging sensor of claim 1, wherein the spectral filter of each pixel of the plurality of pixels in the at least one superpixel has different passbands than the spectral filter of each other pixel of the plurality of pixels in the at least one superpixel.

8. The multispectral imaging sensor of claim 1, wherein the at least one superpixel comprises a plurality of superpixels and each superpixel is the same as each other superpixel.

9. A method of generating a multispectral image using a multispectral imaging sensor, the method comprising:
   projecting a target image on an array of multispectral imaging sensors, each sensor including a plurality of photodetectors and a plurality of spectral filters, each spectral filter attached to a different photodetector to filter light for the photodetector to which it is attached, the spectral filter of each photodetector including at least one wavelength passband, the at least one wavelength passband of each imaging element being different from the at least one wavelength passband of each other photodetector in its sensor;
   filtering spectral information of the image with the plurality of spectral filters each of which includes at least one wavelength passband;
   capturing photons using the photodetectors according to the respective wavelength passband of the spectral filter to which they are attached;
   converting photons to electric charges; and
   reassembling an image for each wavelength passband using a processor based on the electric charges.

10. The method of claim 9, wherein capturing photons using the photodetectors comprises capturing photons with each sensor using photodetectors attached to spectral filters having respective passbands for blue, green, and red spectra of light.

11. The method of claim 10, wherein capturing photons using the photodetectors comprises capturing photons with each sensor using a photodetector attached to a spectral filter having a passband for a near-infra-red (NIR) spectra of light.

12. The method of claim 11 further comprising co-registering the images for the respective wavelength passbands of the photodetectors.

13. A system for multispectral imaging comprising:
   an imaging sensor comprising:
      at least one superpixel including a plurality of pixels, wherein each pixel of the plurality of pixels comprises:
      an imaging element including a plurality of photodetectors; and
      a spectral filter attached to the imaging element, wherein the spectral filter has a plurality of passbands and permits light to pass to only the imaging element to which it is attached only within a plurality of passbands; and
   a computing device communicatively coupled to the imaging sensor and configured to receive electrical signals from each pixel of the imaging sensor and generate an image based on the received electrical signals.

14. The system of claim 13, wherein the plurality of passbands include blue, green, red, and near-infra-red spectra of light.

15. The system of claim 13, wherein the spectral filter of each pixel of the plurality of pixels in the at least one superpixel has different passbands than the spectral filter of each other pixel of the plurality of pixels in the at least one superpixel.

16. The system of claim 13, wherein the spectral filter of each imaging element comprises layers of low dielectric material and high dielectric material alternatively deposited on its imaging element.

17. The system of claim 13, wherein for each pixel the plurality of passbands comprises non-overlapping passbands.

18. The multispectral imaging sensor of claim 1, wherein for each pixel the plurality of passbands comprises non-overlapping passbands.

* * * * *